United States Patent
Schertiger (10) Patent No.: US 9,849,267 B2
(45) Date of Patent: Dec. 26, 2017

(54) COUPLING ARRANGEMENT FOR A TELESCOPIC DEVICE

(71) Applicant: Coloplast A/S, Humlebaek (DK)

(72) Inventor: Lars Olav Schertiger, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 411 days.

(21) Appl. No.: 14/402,691

(22) PCT Filed: May 17, 2013

(86) PCT No.: PCT/DK2013/050149
§ 371 (c)(1),
(2) Date: Nov. 21, 2014

(87) PCT Pub. No.: WO2013/174381
PCT Pub. Date: Nov. 28, 2013

(65) Prior Publication Data
US 2015/0112313 A1    Apr. 23, 2015

(30) Foreign Application Priority Data

May 23, 2012 (DK) ................................ 2012 70275

(51) Int. Cl.
*A61M 25/01*    (2006.01)
*A61M 25/00*    (2006.01)
*A61M 39/10*    (2006.01)

(52) U.S. Cl.
CPC ........ *A61M 25/01* (2013.01); *A61M 25/0017* (2013.01); *A61M 39/1011* (2013.01); *A61M 2025/0175* (2013.01)

(58) Field of Classification Search
CPC .............. A61M 25/0017; A61M 25/01; A61M 2025/0175; A61M 39/1011; A61M 27/008; A61B 2017/00991; A47G 21/189
See application file for complete search history.

(56) References Cited

U.S. PATENT DOCUMENTS

2010/0211049 A1* 8/2010 Schertiger ............. A61M 25/00
                                                      604/544
2011/0077591 A1   3/2011 Plicchi et al.

FOREIGN PATENT DOCUMENTS

| RU | 2294154 C2 | 2/2007 |
|---|---|---|
| WO | 03002179 A2 | 1/2003 |
| WO | 2008138351 A1 | 11/2008 |
| WO | 2008138352 A1 | 11/2008 |
| WO | 2011063816 A1 | 6/2011 |

* cited by examiner

*Primary Examiner* — Gabriella Burnette
(74) *Attorney, Agent, or Firm* — Coloplast Corp., Coloplast A/S; Nick Baumann (57) ABSTRACT

A telescopic device is disclosed and includes a first tubular element having an extension member disposed axially within the first tubular element. The device has a first position where a coupling member is located on a conical first section of the extension member closer to a distal end of the extension member and a third axial position wherein the coupling member is affixed within a grooved receiving section of the extension member.

13 Claims, 3 Drawing Sheets

Fig. 1
Prior Art

COUPLING ARRANGEMENT FOR A TELESCOPIC DEVICE

BACKGROUND

Urinary catheters are used as a tool assisting in the draining of the urinary bladder of persons with reduced or non-existing bladder control. The reduced or non-existing bladder control may either be temporary or permanent, where a temporary loss of bladder control may be caused by trauma, loss of consciousness or illness, as an example. An example of a permanent loss of bladder control may be where a loss of a neural connection between the brain or spinal cord and the urinary bladder occurs due to a trauma to the spinal cord, as is often the case with para- and/or tetraplegics.

One example of a urinary catheter which is widely used for draining urine from the urinary bladder is where a catheter tube is inserted into the urethra of a user and the tip of the catheter tube is maneuvered into the urinary bladder forcing the urethral sphincter open and thus providing a drainage channel from the urinary bladder and out of the body via the catheter tube. There are two types of catheters which are commonly used: the permanent catheter and the intermittent catheter. The permanent catheter is a highly flexible catheter which is inserted into the body by medical professionals and stays there for a long period of time, and the catheter is anchored inside the bladder. The intermittent catheter is usually a single use catheter or a multiple use catheter, which is inserted into the urethra/bladder by the user for immediate drainage of their urinary bladder and is removed from the urethra/bladder subsequent to the drainage. The following disclosure will primarily be concentrated on the intermittent urinary catheter.

There are a number of different types of intermittent catheters which are currently available for the user, such as the SpeediCath™ and EasiCath™ marketed by Coloplast A/S which are conventional one-piece catheter tubes which have an outlet at the distal end which may be used to connect the catheter to a urinary bag for collecting the urine drained from the urine bladder.

Another type of a catheter is disclosed in WO 03/002179 which is a telescopic catheter where one of the telescopic elements is the catheter package and another telescopic element is the catheter member that telescopes from the catheter package. The telescopic catheter is collapsed during storage and transport and extended for insertion into the urethra, providing female users with a compact and discrete catheter which may be used anywhere and without any significant preparation time.

Another type of catheter is disclosed in WO 2008/138351 which discloses a telescopic device having a first tubular member and an extension member having a coupling member that limits the displacement of the extension member within the first tubular member, where the coupling member engages the interior of the first tubular member. This device is a telescopic intermittent catheter, which is also adapted for use by a male user, where the first tubular member and the extension member are adapted in such a way that both telescopic members are adapted to be inserted into the urethra of the user.

Another type of catheter is disclosed in WO 2011/063816 which discloses a telescopic device that may be extended from a collapsed state to an extended state, and optionally may be subsequently collapsed into a collapsed state so as to facilitate discrete disposal of the catheter after use. The telescopic device comprises a first telescopic member and a second telescopic member, where the second telescopic member is displaceably arranged within the first telescopic member in a first and a second axial direction along the longitudinal axis of the first telescopic member, a coupling arrangement for limiting the displacement of the second telescopic member relative to the first telescopic member where the coupling arrangement has a first and a second coupling configuration.

Generally, any reduction of risks of damaging tissue of the human body when inserting and using a telescopic device, such as a catheter, is desirable. For instance, in some cases urinary catheter users apply too much force to the catheter during the catherization or insertion process. This may be painful and cause tissue damage. In order to eliminate or reduce a user's risk of damaging soft tissues of the human body urinary tract when performing a catherization, there is a need for a telescopic device that collapses and with certainty becomes un-usable if too much resistance against the insertion of the device is encountered, such that a user is prevented from inflicting damage on the body tissue and/or from re-using the device in any subsequent insertion attempts and also provides a simpler solution for mass production.

SUMMARY OF THE INVENTION

According to the invention, a telescopic device comprising a first tubular element and an extension member is provided, where the extension member is displaceably arranged in an axial direction within the first tubular element and wherein a coupling member is provided movably on the extension member and is positionable in first, second and third axial positions. In the first axial position, the extension member can be extracted from the first tubular element so as to bring the telescopic device into a use configuration, in the second axial position the parts of the telescopic device are locked in relation to each other enabling use of the device, and if the coupling member is moved to the third axial position the telescopic device collapses and becomes un-usable because the parts are no longer locked in relation to each other, thereby providing an improved security against unintended re-use of the telescopic device. Detailed Description of the Invention The invention relates to a telescopic device comprising a first tubular element and an extension member, said extension member having a first diameter and being displaceably arranged in an axial direction within the first tubular element, wherein a coupling member is provided movably on the extension member and being positionable in at least,

- a first axial position wherein the extension member is displaceable within the first tubular element,
- a second axial position wherein the coupling member engages between the extension member and the interior of the first tubular element limiting displacement in at least one longitudinal direction, and
- a third axial position wherein the coupling member is fixated relative to the extension member by a receiving section of the extension member having a second diameter of less than said first diameter.

It should be understood within the meaning of the present invention that the term "engage" can mean to interlock or cause interlocking between two parts. Furthermore, the terms "displaceable" and "movably" mean to be able to move from one position to another position. The limited displacement referred to concerns the displacement of the extension member in relation to the first tubular element or vice versa.

It should be understood within the meaning of the present invention that the term "interior" can mean any part of the first tubular element, which cannot be construed as facing the exterior of the first tubular element. This may include the inner surface of the tubular element, any form of groove or extrusion on the inside of the tubular element or any surface area that is not facing the exterior or the outside of the tubular element, e.g. facing inwards and towards the central longitudinal axis of the first or the second tubular element.

Within the meaning of the present invention, it should be understood that the extension member may have more than a first and a second diameter along the length of its longitudinal extent. One example could be that the proximal end of the extension member may taper towards a smaller diameter at its tip, but in principle the extension member can have any number of individually distinct diameters according to needs. The first diameter referred to may also be an average or mean value of a number of individually distinct or varying diameters of the extension member.

Within the meaning of the present invention, it should be understood that the term "fixated" means that when positioned in the third axial position, the coupling member is prevented from displacement or movement in relation to the extension member.

It is preferred that the coupling member is not palpable or cannot be felt through the walls of the first tubular element by running the fingers across the outer surface of the first tubular element. This is advantageous in that the coupling member cannot be felt and does not injure or damage anatomical structures in the body of a user when the telescopic device is inserted into the urethra of the user.

It should be understood that the coupling member and the extension member are capable of relative placement in more than the first, second and third axial positions. Thus, there may for example be many intermediate positions between the first and second axial position, however no intermediate positions between the second and third axial position.

When the coupling member is positioned in the first axial position or in any intermediate position between the first and second axial position, the extension member may be axially displaced relative to (and within) the first tubular element. A user may apply a pulling force to the extension member by applying pressure to the outer surface of the extension member, e.g. using the fingers of the hand directly or indirectly using a non-touch applicator, and pulling the extension member in a direction out of the first tubular element, or by applying pulling or pushing force in the opposite direction, in a direction towards the first tubular element.

When the coupling member is positioned in the second axial position, the coupling member engages between the extension member and the interior of the first tubular element thereby limiting displacement in at least one longitudinal direction. The second axial position of the coupling member generally corresponds to the situation wherein the extension member is in its maximum extent in relation to the first tubular element, i.e. when the extension member has been pulled out of the first tubular element. When the coupling member is in this second axial position, it limits the displacement of the extension member in at least one longitudinal direction, typically preventing the extension member from being moved in the direction towards the first tubular element.

Thus, in a case where the telescopic device is a urinary catheter, the device may be arranged in an extended state, for insertion of the catheter into the urinary channel, and during the insertion, the telescopic urinary catheter will be maintained in its extended state without being collapsed or reduced in length under normal use circumstances.

In the third axial position, the coupling member is fixated relative to the extension member by a receiving section of the extension member having a second diameter less than a first diameter of the extension member. Thus, when in this position, the coupling member is prevented from movement, i.e. it is not able to be moved or displaced, in relation to the extension member. This has the consequence that the coupling member no longer limits displacement of the extension member in any longitudinal direction of the telescopic device.

Particularly, in embodiments where the telescopic device is a telescopic urinary catheter, the provision of a coupling member being positionable in a third axial position, in which it is fixated in relation to the extension member, means that a telescopic urinary catheter having security against self-inflicted tissue damage is achieved. If a user tries to catheterize himself with a telescopic urinary catheter according to embodiments of the invention, and the application force the exerts on it exceeds a pre-determined threshold, the coupling member positions itself in the third axial position and eliminates the possibility and/or effects of any continued application of force, since the extension member is no longer limited in displacement in any longitudinal direction. Thereby, the risk of damaging the soft tissues of the urinary channel is eliminated or significantly reduced.

Moreover, when the coupling member is in the third axial position, it results in a collapse of the telescopic device in the sense that the telescopic device becomes un-usable. Thus, a user cannot unintentionally or deliberately use the device a second time as it has lost its functionality. In other words, if the coupling member is in the third axial position, it is possible for the user to move the extension member back and forth, or in and out, in relation to the first tubular element. The extension member can thus be displaced back to a position corresponding in practice to its initial position before use.

Moreover, in the third axial position of the coupling member of a telescopic urinary catheter according to embodiments of the invention, the catheter has lost its functionality, thus ensuring that no unintended and potential bacterial infection inflicting second catherization attempts are possible. The feature that the extension member can be pushed fully back into the first tubular element is particularly advantageous in the case of a telescopic urinary catheter, as there is no possibility of the telescopic catheter remaining extended, or remaining partly extended in an intermediate position of the coupling member, which could otherwise suggest to a user that the telescopic urinary catheter could be capable of repeated use.

Furthermore, as the extension member can be pushed fully back into the first tubular element, the third axial position of the coupling member also provides the possibility that the user may intentionally collapse the used catheter after a normal catheterization procedure. By exposing the extension member to a force over the pre-determined threshold, the user can collapse the catheter and reduce it to its original size. Indeed, the catheter may then for the sake of example be put back into its packaging to be disposed of as a single piece of waste. This provides a more discrete catheter product, also after use.

In embodiments of the invention, the receiving section of the extension member is provided as a groove. It is therefore to be understood that the receiving section of the extension member is a groove of a certain extent provided by a part of the extension member having a second diameter that is smaller or less than a first diameter of the extension member. The groove ensures that the coupling member can be fixated in relation to the extension member and does not contact the inner surface of the first tubular element such that the extension member can be moved or displaced in the direction of the first tubular element (or vice versa) without encountering any (or very little) frictional resistance to the movement caused by contact between the coupling member and the inner surface of the first tubular element.

In embodiments of the invention, the groove is sized to accommodate the coupling member. In this way, the groove can receive the coupling member fully thereby improving the fixation of the coupling member relative to the extension member. Thus, depending on the size of the coupling ring, the second diameter of the extension member may be adapted according to requirements based on the dimensions of the coupling member.

In embodiments of the invention, the groove has approximately the same width as the coupling member as viewed in the longitudinal direction of the telescopic device. In this way, the groove can receive the full width of the coupling member to obtain a good fixation of the coupling member relative to the extension member without accommodating the coupling member fully, thereby facilitating other adaptation possibilities for the second diameter of the extension member.

In embodiments of the invention, a transition part between the first and second diameters of the extension member is provided as a straight line perpendicular to the longitudinal direction of the extension member. In other words, the transition between the two diameters is abrupt and there is no subpart or section of the transition part that is tapered or sloping. In embodiments where the receiving section is a groove, this means that the transition part may constitute an end part that can be considered an end wall of the groove, the end wall being perpendicular to the longitudinal direction of the extension member. This ensures that the coupling member is securely fixated in the third axial position and cannot unintentionally be displaced from that position once it is positioned there.

In embodiments of the invention, the coupling member is arranged around a conical shaped surface area of the extension member tapering along the axial direction between the first and second axial positions of the coupling member. Thus, by sliding the coupling member along the conical shaped surface area it can, in a simple way, be moved between its first axial position and its second axial position.

In embodiments of the invention, the coupling member is a coupling ring having an inner surface facing the extension member and an outer surface facing the first tubular element.

It should be understood that reference to outer and inner surfaces of the different elements of the invention and as described herein should be seen with respect to a longitudinal axis of the telescopic device. Thus, surfaces facing out and away from the axis of the telescopic device are referred to as outer surfaces, while surfaces facing inwards and towards the axis are referred to as inner surfaces.

In embodiments of the invention, the inner surface of the coupling ring is sloping. Particularly, but not exclusively, the slope may correspond and be equal to the slope of the conical shaped surface of the extension member tapering along the axial direction as described above. In other words, the inner surface of the coupling ring and the conical shaped surface area of the extension member have the same conicity. This has the effect that all of the inner surface of the coupling ring may contact the (outer) conical surface area of the extension member. Thereby an improved guidance and/or control of the coupling ring is achieved because the whole area of the inner surface of the coupling member is in sliding contact engagement with the conical shaped surface area of the extension member.

Thus, in embodiments, all of the inner surface area of the coupling member is contacting the conical shaped surface area of the extension member. This further increases the security for achieving a correctly functioning locking mechanism for the telescopic device. Even further, the embodiments according the present invention provide a less complicated and therefore more cost efficient design and also allow for larger manufacturing tolerances during production.

In embodiments of the invention, a radial extent of the coupling ring is variable from a first radial extent in the first axial position to a second radial extent in the second axial position and to a third radial extent in the third axial position, where the radial extent of the coupling ring is larger in the second radial extent than in the first or third radial extent. The term "variable" regarding the radial extent of the coupling ring means that the radius of the ring may be expanded and/or reduced.

When the coupling ring is moved to its second axial position, the second axial extent of the ring is larger than the first axial extent and an outer surface of the coupling ring is pressed against the inner surface of the first tubular element, providing a tight frictional grip. In the third axial position, the third axial extent of the coupling ring is less than in the second axial position. Thus, in the third axial position, the outer surface of the coupling ring may or may not be in contact with the inner surface of the first tubular element. However if there is contact between the parts, any resulting frictional grip is insignificant and does not prevent the telescopic device from being collapsed. Preferably, there is no contact between the outer surface of the coupling ring and the inner surface of the first tubular element. Thus, the extension member can be moved in and out of the first tubular element without encountering any resistance.

In order to achieve a particularly desired value or size of the frictional grip, in embodiments the coupling ring is deformable. The coupling ring may be formed of a deformable and/or compressible material. Other physical material characteristics such as material elasticity and friction coefficient may also be important parameters of a coupling ring material.

In embodiments of the invention, the coupling ring is formed of a high friction material. A high friction material should be understood as a material, which when the coupling ring is pressed against the first tubular element in its second axial position provides a high coefficient of friction. Such coefficient of friction is not absolute and may be altered for different embodiments. Thus, in one embodiment, it can be above 0.1, however it could be above 0.2 or even 0.3. In embodiments where the telescopic device is a telescopic urinary catheter, these values should be considered in view of the coefficient of friction between a coated catheter and the urethra, which may be as low as between 0.03 and 0.01.

In embodiments of the invention, the inner surface of the coupling ring is provided with a low friction surface. Thereby, it is to be understood that the coupling ring itself may be wholly or partly made from a high friction material while its inner surface may be a low friction surface, e.g. achieved by an easy-slip type of coating.

In embodiments of the invention, the outer surface of the coupling member is provided with at least one rib. Such ribs provide a small contact area against the inner surface of the first tubular element, which results in a correspondingly higher pressure between the rib and the inner surface than if the whole surface of the coupling ring distributes the pressure.

Additionally, such ribs, or the whole coupling member can be formed of a relatively hard material compared to the first tubular element. Thereby, the ribs dig into, cut into or deform inwardly the inner surface of the first tubular element providing a very secure engagement.

In embodiments of the invention, the outer surface of the coupling member is provided with a high friction surface.

In embodiments of the invention, the outer surface of the coupling member is provided with treads.

In embodiments of the invention, the coupling ring is formed as an open ring, having a c-shape when viewed in cross section. This shape allows for the coupling ring to be easier deformed when the coupling ring is formed of a hard material, as the opening in the c-shape will allow for the ring to be pressed together until the ends of the c-shape meet, providing a small enveloping circumference. Similarly, it allows for the ring to be opened, i.e. the ends of the c-shape are moved away from each other providing a large enveloping circumference.

In embodiments of the invention, the surface area of the receiving section on the extension member is parallel with the inner surface of the first tubular element. Thus, when the coupling member is moved to its third axial position and enters the receiving section it does not slide on, or contact, the conical shaped surface area of the extension member. In the receiving section of the extension member, the coupling member is fixated relative to the extension member and is thus prevented from further movement in relation thereto.

In embodiments wherein the coupling member is a coupling ring and the inner surface thereof is sloping, the inner surface of the coupling ring only contacts the surface area of the receiving section over a small area. This is because the sloping inner surface and the surface area of the receiving section are at an angle to each other (corresponding to the slope or conicity of the inner surface of the coupling ring). In fact, the mentioned surfaces may only contact in a point (or circle if viewed along the circumference of the extension member).

As introduced, the transition between the conical shaped surface area and the parallel surface area of the receiving section may be provided as a straight line perpendicular to the longitudinal direction of the extension member. The transition may be a transition between first and second diameters of the extension member, said first diameter depending on where it is measured on the axial extent of extension member, which may e.g. be on the conical surface area. The second diameter of the extension member may correspond to the diameter of the extension member in the surface area of the receiving section.

Thus, particularly in embodiments of the invention comprising a c-shaped coupling ring, if the coupling ring is moved to the third axial position and thus received in the receiving section of the extension member, it is securely fixated therein which has the effect that the c-shaped coupling ring cannot be heeled or everted over/past the transition between the conical shaped surface area and the parallel surface area of the receiving section. This is because the transition is abrupt and does not provide any tapering or sloping surface for the coupling ring to initially slide on. This eliminates any risk of a user being able to bring the telescopic device into the use configuration again after the pre-determined threshold value has been exceeded. This is particularly an advantage in embodiments wherein the telescopic device is an intermittent urinary catheter.

In embodiments of the invention, the conical shaped surface area and the receiving section surface area are provided on a separate bushing element attached to the distal end of the extension member.

The bushing element may comprise first and second annular rims. One or both of the annular rims may be dimensioned to allow frictional engagement between the bushing element and the inner surface of the first tubular element and/or to control the movement of the extension member inside the first tubular element. The annular rims also provide stops for the movement of the coupling element. The bushing element may also comprise a neck portion extending into the extension member. The outer surface of the neck portion contacts the inner surface of the extension member. The outer surface of the neck portion of the bushing element is attached to the extension member either by frictional forces or by mechanical fastening such as gluing or welding. However, other ways of attaching the bushing element to the extension member, such as attaching the bushing element to a distal-most portion of the extension member, may be applied as long as a secure (non-leaking) fluid connection between the parts is established.

In embodiments, the coupling member or coupling ring and the bushing element may be made of two different materials allowing further possibilities of differentiating the frictional forces between the two parts.

In embodiments of the invention, the bushing element is formed with a through-going opening along the axial direction. This, for example, allows for communication between passageways in the telescopic device in embodiments, wherein the extension member is a second tubular element.

In embodiments, the telescopic device is a telescopic intermittent urinary catheter.

Such embodiment may for example cover telescopic devices such as a telescopic intermittent urinary catheter, wherein the first tubular element can be the distal section and the second tubular element can be the proximal section. This allows urine to flow through both telescopic sections, typically from the bladder through the proximal section and out through the distal section.

In embodiments, it may be desirable to use a different material for the conical shaped surface area than that used to form the extension member in order to achieve different properties and/or for manufacturing reasons. In embodiments of the invention, the conical shaped surface area is provided with a low friction surface, e.g. provided as a coating.

In embodiments of the invention, the frictional force $F_1$, between the inner surface of the tubular element and the outer surface of the coupling member, is larger than the frictional force $F_2$, between the inner surface of the coupling member and the extension member.

In embodiments, the telescopic device collapses and becomes un-usable if a reaction force incurred on the extension member and working in the direction of the first tubular element exceeds a pre-determined threshold value of the force.

BRIEF DESCRIPTION OF THE DRAWING

The invention will be discussed further with reference to the following illustrative drawings, wherein.

DETAILED DESCRIPTION OF THE DRAWING

Figure 1:
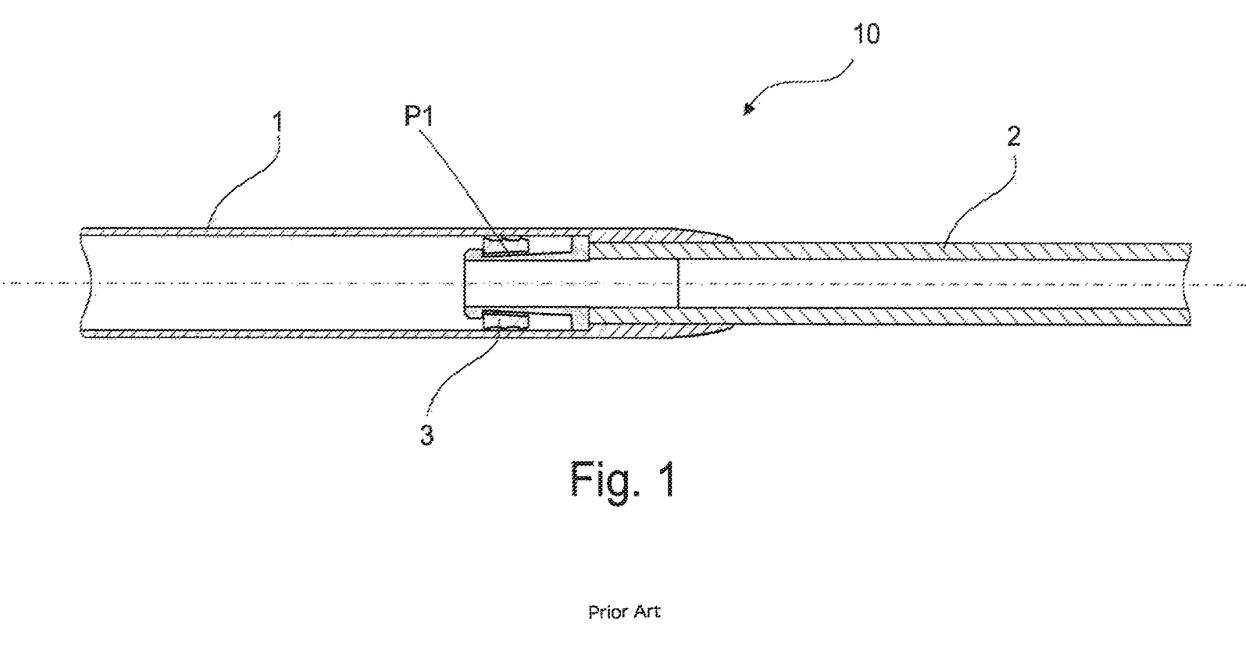
FIG. 1 is an illustrative cross-section of a telescopic device having a coupling member according to the prior art.

FIG. 1 shows a prior art telescopic device 10 comprising a distal tubular element 1 and a proximal extension member 2. A distal part of the extension member 2 is provided as a tapering section around which a coupling member 3 in the form of a coupling ring is provided. The coupling ring is shown in a first axial position P1. The extension member 2 of the telescopic device 10 is shown in a situation where it is maximally retracted from the distal tubular element 1. If the telescopic device 10 is inserted by pushing it into a cavity or conduit-like entity, e.g. an anatomical opening in a human or animal body, the proximal end of the extension member 2 may encounter an obstacle in said cavity causing a reaction force to work on the telescopic device (primarily the proximal tip of the extension member 2 (not shown)); this force in turn attempts to push the extension member 2 back into the distal tubular element 1. This movement causes the coupling member 3 to slide on the tapering section of the extension member forcing the outer surface of the coupling member into frictional contact with the inner surface of the distal tubular element. Thereby, it is ensured that the telescopic device 10 is locked in its extended form and cannot collapse.

Figure 2A:
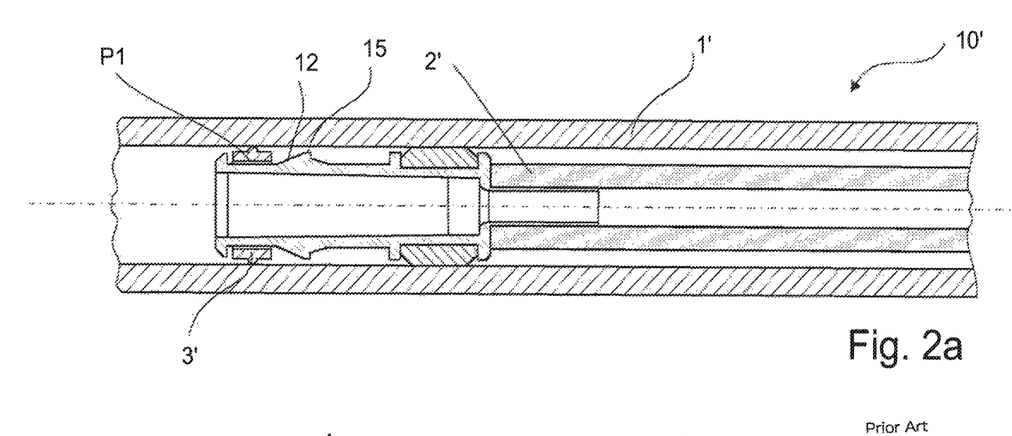
FIG. 2a is an illustrative cross-section of a telescopic device having a coupling member according to another example of the prior art, showing the coupling member in a first axial position.
Figure 2B:
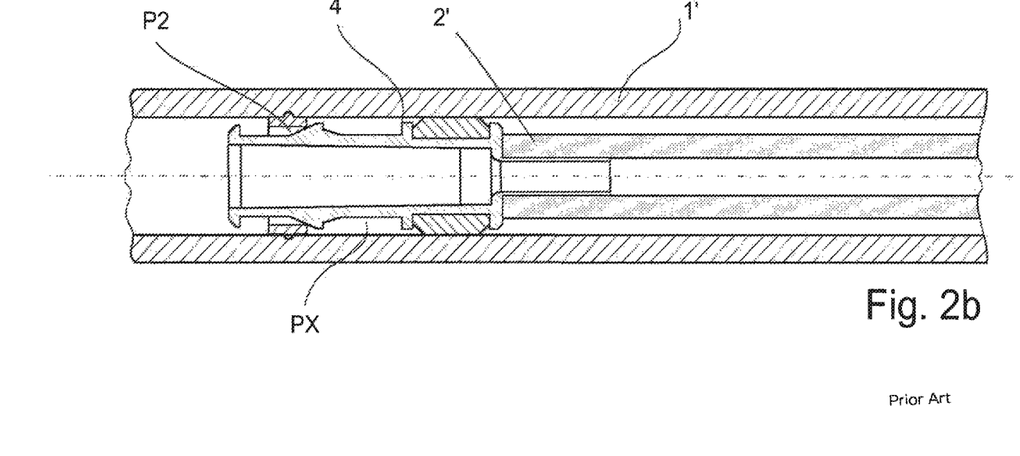
FIG. 2b is an illustrative cross-section of the prior art telescopic device according to FIG. 2a, showing its coupling member in a second axial position.

FIGS. 2a and 2b show another example of a prior telescopic device 10' having a coupling member 3' with an inner surface parallel to the longitudinal axis of the extension member 2'. In the shown example, the extension member 2' is not fully extracted from the distal tubular element 1'. In FIG. 2a, the coupling member 3' is shown in an axial position P1 on the extension member 2' corresponding to its position during retraction of the extension member 2' from the distal tubular element 1'.

In FIG. 2b, the coupling member 3' is shown in a second axial position P2 on the extension member 2', corresponding to its position if a force is working on the extension member 2' in a direction attempting to push it towards the distal tubular element 1'.

During normal use of the telescopic device, this position P2 of the coupling member 3' on the extension member 2' prevents the extension member 2' from moving further in the direction of the distal tubular element 1', because of the friction between the outer surface of the coupling member 3' and the inner surface of the distal tubular element 1'. However, if the extension member 2' is submitted to a substantial force pushing it in the direction of the distal tubular element 1', the coupling member 3' may slide on the tapering surface 12 of the extension member 2' and move past (the force required is subject to dimensions and materials of the coupling member and the distal tubular element) the ridge 15, and may then be positioned in any axial position PX on the extension member 2' between the ridge 15 and the annular rim 4. If the extension member 2' is continuously submitted to force working in the direction of the distal tubular element 1', the extension member 2' may consequently be pushed back into the distal tubular element 1'. However, the extension member 2' can no longer move in the opposite direction and be extracted from the distal tubular element 1' again, because the coupling element 3' will slide back and abut the ridge 15. However, this construction is left with a risk of a user being able to twist or evert the coupling member 3' past the ridge 15 as the coupling member 3' is not securely fixated in relation to the extension member after the application of the substantial force.

Figure 3A:
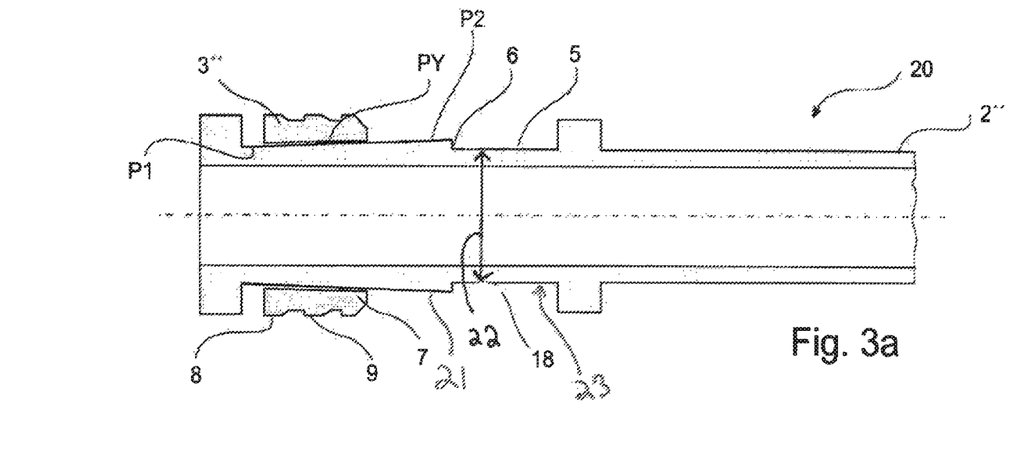
FIG. 3a is an illustrative cross-section of a distal end part of an extension member of a telescopic device according to the present invention having a coupling member and showing the coupling member in a first axial position.
Figure 3B:
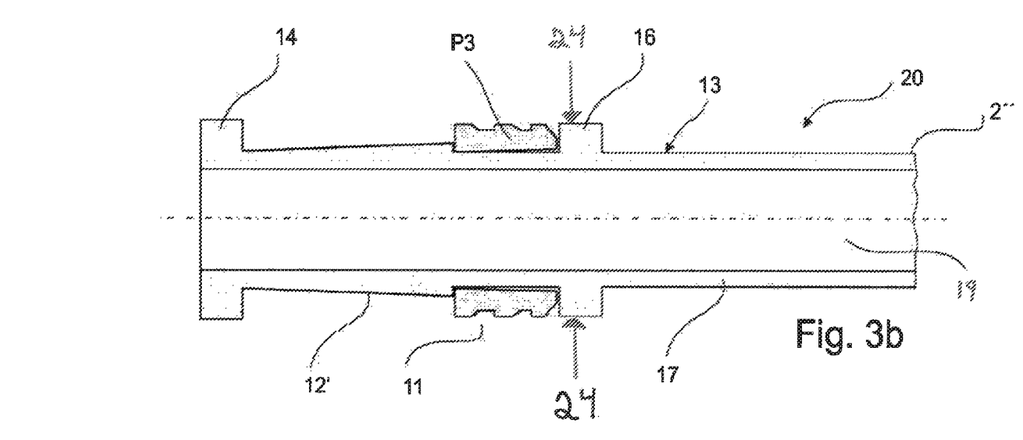
FIG. 3b is an illustrative cross-section of a distal end part of an extension member of a telescopic device according to the present invention having a coupling member and showing the coupling member in a third axial position.

FIGS. 3a and 3b show the distal end part of the extension member 2" of a telescopic device 20 according to the invention. The first tubular element is not shown. The extension member comprises a conical surface area 12' (a first section 21) around which the coupling member 3" is movably provided to move between a first P1 and a second P2 axial position through any intermediate axial position PY therebetween (coupling member 3" only shown in position PY in FIG. 3a). The coupling member 3" may also move into a third axial position P3 (FIG. 3b) in a receiving section 5 on the extension member 2" having a surface area 18 (having a second diameter 22) that is parallel with the inner surface of the first tubular element, and from which position the coupling member 3" cannot be moved further. In FIG. 3a, the coupling member 3" is in an intermediate axial position PY, and in FIG. 3b the coupling member 3" is in the third axial position P3 and thus received in the receiving section 5.

The receiving section 5 on the extension member 2" is shown in the form of a groove 23. The coupling member 3" has a sloping inner surface area 7 all of which is contacting the conical shaped surface area 12' of the extension member 2" and an outer surface 8 for frictional engagement with the inner surface of the first tubular element (not shown). The slope or conicity of the inner surface area 7 and the conical shaped surface area 12' is shown as being identical. For the sake of example, the outer surface 8 of the coupling member 3' is shown with ribs 9 and treads 11, both features that may be applied to control the degree of frictional engagement between the device parts. The transition 6 between the conical shaped surface area 12' and the parallel surface area 18 is shown as a straight line perpendicular to the longitudinal direction of the extension member 2" thus making the transition abrupt.

FIG. 3b further shows how the inner surface 7 contacts the surface area 18 of the receiving section 5 in the third axial position P3 in which the inner surface 7 of the coupling member 3" only contacts the surface area 18 over a small area. This is because the sloping inner surface 7 and the surface area 18 of the receiving section 5 are at an angle to each other. As can be seen, the surfaces may only contact in a point closest to the transition (or the area of contact is a circle if considered along the circumference of the receiving section 5 of the extension member 2").

The conical surface area 12' and the parallel surface area 18 may be provided on a separate bushing element 13 having a neck portion 17 that may be inserted into the distal end of the extension member of the telescopic device. The bushing element 13 has first and second annular rims 14, 16, the second annular rim 16 has a rim diameter 24 and may abut against a distal end of the extension member (not shown). The outer surface of the neck portion 17 engages the inner surface of the extension member. The bushing element 13 has a through-going passageway 19 allowing fluid to move through the bushing element from the extension member to the first tubular element.

According to the invention, when the extension member 2" is extracted from the first tubular element, the coupling member 3" will be in the first axial position corresponding to the coupling member 3" abutting the first annular rim 14 thereby providing little or no resistance to the extraction movement, as the outer surface 8 of the coupling member 3" is in no or very little frictional engagement with the inner surface of the first tubular element.

When the extension member 2" has been extracted from the first tubular member, the telescopic device 20 is ready for use. In specific embodiments, the device is a telescopic urinary catheter for entering through the urethra into the bladder to be able to void urine from the bladder. To do this, the user will insert the proximal end of the extension member 2" into the urethra and continue the insertion of the catheter until it has entered into the bladder and urine starts to flow through the extension member 2" into the first tubular element, and from the distal end of the first tubular element into a collecting device or a toilet.

If during insertion of the catheter an obstacle is encountered, the reaction force from this encounter will cause the extension member 2" to move in the direction of the first tubular element. This in turn causes the coupling member 3" to start sliding on the conical surface area 12' of the extension member 2". If the user continues to move the catheter into the urethra, the frictional engagement between the outer surface 8 of the coupling member 3" and the inner surface of the first tubular element will increase, thereby allowing the user to continue with the insertion of the catheter as the extension member 2" is not pushed back into the first tubular element.

However, if the reaction force working on the extension member 2" in the direction towards the first tubular element exceeds a pre-determined value that is substantially higher than a usual force required for inserting a urinary catheter, the coupling member 3" will move past the transition 6 and into the receiving section 5, thereby moving into its third axial position P3. The diameter of the extension member 2" (or the separate bushing element 13) in the receiving section or groove 5 in the third axial position P3 of the coupling element 3" is less than a first diameter of the extension member 2" (e.g. measured on the conical surface area immediately adjacent the transition).

According to the invention, once moved to the third axial position P3, the coupling member 3" cannot be moved further. Thereby, the extension member 2" will be able to move freely (or with very little resistance) inside the first tubular element in both a distal and a proximal direction as there is no frictional engagement between the coupling member 3" and the inner surface of the first tubular element. Thus, in embodiments where the telescopic device is an intermittent urinary catheter, the catheter is thereby collapsed and the risk of a user trying to re-use it is eliminated. Furthermore, any risk of forcing the coupling member 3" back into a use-enabling position PY is also eliminated because the coupling member 3" is securely fixated in relation to the extension member 2".

The invention claimed is:

1. A telescopic device comprising:
   a first tubular element;
   an extension member disposed axially within the first tubular element, the extension member having a first annular rim located at a distal end of the extension member and a second annular rim located between the first annular rim and a proximal end of the extension member, with the extension member provided with a rim diameter measured at an outer periphery of the second annular rim, and with the extension member having a first section extending from the first annular rim to a receiving section, and the receiving section extending from the first section to the second annular rim; and
   a coupling member movable relative to the extension member and coupled to the extension member between the first annular rim and the second annular rim, the coupling member is positionable in at least:
   a first axial position wherein coupling member is located on the first section of the extension member closer to the first annular rim than to the second annular rim such that the extension member is displaceable within the first tubular element,
   a second axial position wherein the coupling member is located on the first section of the extension member closer to the second annular rim than to the first annular rim such that the coupling member engages between the extension member and an interior of the first tubular element limiting displacement of the extension member in at least one longitudinal direction, and
   a third axial position wherein the coupling member is affixed within the receiving section of the extension member, wherein the receiving section has an outside second diameter that is less than the rim diameter.

2. A telescopic device according to claim 1, wherein the receiving section of the extension member is a groove located between the first section and the second annular rim, with the groove having a constant diameter that is equal to the outside second diameter.

3. A telescopic device according to claim 2, wherein the groove has a length that is sized to receive an entirety of a length of the coupling member.

4. A telescopic device according to claim 1, wherein a transition is formed as a perpendicular wall between the first section and the receiving section.

5. A telescopic device according to claim 1, wherein the first section is a conical surface area of the extension member that is tapered to diverge along the axial direction from the first annular rim toward the second annular rim.

6. A telescopic device according to claim 1, wherein the coupling member is a coupling ring having an inner surface facing the extension member and an outer surface facing the first tubular element.

7. A telescopic device according to claim 6, wherein the inner surface of the coupling ring is sloped at an angle and the first section is sloped at the same angle.

8. A telescopic device according to claim 7, wherein the coupling ring is formed as an open C-shaped ring.

9. A telescopic device according to claim 1, wherein a surface area of the receiving section on the extension member is parallel with an inner surface of the first tubular element.

10. A telescopic device according to claim 9, wherein the first section and the receiving section are provided on a separate bushing element attached to the extension member.

11. A telescopic device according to claim 10, wherein the bushing element is formed with a through-going opening along the axial direction.

12. A telescopic device according to claim 1, wherein the telescopic device is a telescopic intermittent urinary catheter.

13. A telescopic device according to claim 12, wherein the first tubular element is a distal section and the telescopic intermittent urinary catheter has a proximal section that is adapted to be insertable into a urethra of a user of the intermittent urinary catheter.

\* \* \* \* \*